(12) United States Patent
Hair

(10) Patent No.: US 8,734,407 B2
(45) Date of Patent: May 27, 2014

(54) FACETED NASAL SEAL

(75) Inventor: Kenneth A. Hair, Fort Collins, CO (US)

(73) Assignee: Water Pik, Inc., Fort Collins, CO (US)

( * ) Notice: Subject to any disclaimer, the term of this patent is extended or adjusted under 35 U.S.C. 154(b) by 0 days.

(21) Appl. No.: 13/424,418

(22) Filed: Mar. 20, 2012

(65) Prior Publication Data
US 2012/0179118 A1 Jul. 12, 2012

Related U.S. Application Data

(60) Division of application No. 12/970,854, filed on Dec. 16, 2010, now Pat. No. 8,409,152, and a continuation-in-part of application No. 29/364,669, filed on Jun. 25, 2010, now Pat. No. Des. 676,125, and a continuation-in-part of application No. 29/364,670, filed on Jun. 25, 2010, now Pat. No. Des. 676,126.

(60) Provisional application No. 61/369,378, filed on Jul. 30, 2010.

(51) Int. Cl.
A61M 31/00 (2006.01)
B65D 37/00 (2006.01)
A61M 11/00 (2006.01)
A61M 15/08 (2006.01)
A61M 3/02 (2006.01)

(52) U.S. Cl.
CPC ............. *A61M 15/08* (2013.01); *A61M 3/0262* (2013.01); *A61M 3/0279* (2013.01); *A61M 2011/008* (2013.01); *A61M 2210/0618* (2013.01)
USPC ........................ 604/275; 222/211; 128/200.14

(58) Field of Classification Search
CPC . A61M 15/08; A61M 3/0262; A61M 3/0279; A61M 2210/0618; A61M 2011/008
USPC ........ 604/36, 37, 93.01, 94.01, 275; 222/211; 128/200.14
See application file for complete search history.

(56) References Cited

U.S. PATENT DOCUMENTS

| 465,559 A | 12/1891 | Good |
| 2,115,959 A | 5/1938 | Lewis |
| 2,571,921 A | 10/1951 | Morris |

(Continued)

FOREIGN PATENT DOCUMENTS

| DE | 29602605 | 4/1996 |
| GB | 881807 | 10/1958 |
| WO | WO96/29044 | 9/1996 |
| WO | WO2005/000477 | 1/2005 |

OTHER PUBLICATIONS

Waterpik SinuSense, Website: http://www.insightsbyapril.com/2012/03/waterpik-natural-remedy-for-sinus.html, retrieved on May 31, 2012.

(Continued)

*Primary Examiner* — Aarti B Berdichevsky
(74) *Attorney, Agent, or Firm* — Dorsey & Whitney LLP

(57) ABSTRACT

A nozzle for a nasal rinse device including a collar that forms a conduit. The collar is configured to attach the nozzle to the nasal rinse device. An outlet aperture defined by the collar is on a top portion of the nozzle. The nozzle also includes a skirt extending outwards and downwards from the collar, and an outer surface of the skirt is faceted.

21 Claims, 11 Drawing Sheets

(56) References Cited

U.S. PATENT DOCUMENTS

| | | |
|---|---|---|
| 2,578,864 A | 12/1951 | Tupper |
| D169,996 S | 7/1953 | Vuillement |
| 2,722,458 A | 11/1955 | Wahlin |
| 2,811,283 A | 10/1957 | Bowen |
| 2,987,261 A | 6/1961 | McCuiston et al. |
| 3,176,883 A | 4/1965 | Davis, Jr. |
| 3,363,808 A | 1/1968 | Gorman |
| 3,455,294 A | 7/1969 | Adler et al. |
| 3,820,532 A | 6/1974 | Eberhardt et al. |
| 3,847,145 A | 11/1974 | Grossan |
| 4,083,840 A | 4/1978 | Schoefberger |
| D250,546 S | 12/1978 | Pick et al. |
| D250,601 S | 12/1978 | Pick et al. |
| 4,179,051 A | 12/1979 | Thomas |
| 4,356,941 A | 11/1982 | McRoskey et al. |
| D271,028 S | 10/1983 | Adams |
| 4,410,110 A | 10/1983 | Del Bon et al. |
| 4,439,206 A | 3/1984 | Hildebrand et al. |
| 4,489,535 A | 12/1984 | Veltman |
| 4,513,891 A | 4/1985 | Hain et al. |
| 4,526,797 A | 7/1985 | Stone, Jr. |
| 4,555,469 A | 11/1985 | Erdmann et al. |
| 4,760,937 A | 8/1988 | Evezich |
| D305,262 S | 12/1989 | Nichols |
| 4,925,128 A | 5/1990 | Brody |
| D314,702 S | 2/1991 | Gonzalez |
| D317,940 S | 7/1991 | Brenner |
| 5,301,846 A | 4/1994 | Schmitz |
| 5,316,054 A | 5/1994 | Hall et al. |
| 5,330,634 A | 7/1994 | Wong et al. |
| 5,354,849 A | 10/1994 | Schoefberger |
| 5,505,193 A | 4/1996 | Ballini et al. |
| 5,570,966 A | 11/1996 | Phelan |
| 5,611,376 A | 3/1997 | Chuang |
| 5,649,530 A * | 7/1997 | Ballini .................... 128/200.14 |
| 5,655,686 A | 8/1997 | Jermyn |
| D390,744 S | 2/1998 | Otero |
| 5,806,723 A | 9/1998 | DuBose |
| D405,525 S | 2/1999 | Barrett et al. |
| 5,897,872 A | 4/1999 | Picciano |
| 5,899,878 A | 5/1999 | Glassman |
| 5,967,377 A | 10/1999 | Glynn |
| 6,006,952 A | 12/1999 | Lucas |
| 6,035,769 A | 3/2000 | Nomura et al. |
| D424,197 S | 5/2000 | Sydlowski et al. |
| D426,300 S | 6/2000 | Conforti |
| 6,135,358 A | 10/2000 | Ballini |
| 6,238,377 B1 | 5/2001 | Liu |
| 6,241,705 B1 | 6/2001 | Ko-Wen |
| 6,293,436 B2 | 9/2001 | Faughnder et al. |
| 6,520,384 B2 | 2/2003 | Mehta |
| 6,540,718 B1 | 4/2003 | Wennek |
| 6,558,344 B2 | 5/2003 | McKinnon et al. |
| D481,794 S | 11/2003 | Krinsky |
| 6,669,059 B2 | 12/2003 | Mehta |
| D486,066 S | 2/2004 | Hannen et al. |
| 6,688,497 B2 | 2/2004 | Mehta |
| 6,736,792 B1 | 5/2004 | Liu |
| D490,896 S | 6/2004 | Bogazzi |
| D493,888 S | 8/2004 | Reschke |
| D495,954 S | 9/2004 | Solomon |
| D497,107 S | 10/2004 | Hama et al. |
| 6,814,259 B1 | 11/2004 | Foster et al. |
| 6,907,879 B2 | 6/2005 | Drinan et al. |
| 6,976,669 B2 | 12/2005 | Van Zijll Langhout et al. |
| D530,815 S | 10/2006 | Murphy et al. |
| D538,474 S | 3/2007 | Sheppard et al. |
| D548,334 S | 8/2007 | Izumi |
| D550,097 S | 9/2007 | Lepoitevin |
| 7,306,121 B2 | 12/2007 | Ophardt et al. |
| D558,509 S | 1/2008 | Bodum |
| D558,510 S | 1/2008 | Bodum |
| D562,404 S | 2/2008 | Jansen et al. |
| D584,151 S | 1/2009 | Murphy |
| 7,500,584 B2 | 3/2009 | Shutz |
| D590,493 S | 4/2009 | Harlan et al. |
| D601,697 S | 10/2009 | Sobiech et al. |
| D603,708 S | 11/2009 | Handy |
| D608,645 S | 1/2010 | Handy et al. |
| D612,736 S | 3/2010 | Pecora |
| D613,601 S | 4/2010 | Yoneda |
| 7,703,696 B2 | 4/2010 | Eddins et al. |
| D627,458 S | 11/2010 | Bisson et al. |
| D629,884 S | 12/2010 | Stephens |
| D630,314 S | 1/2011 | Stephens |
| 7,862,536 B2 | 1/2011 | Chen et al. |
| D634,213 S | 3/2011 | Thompson |
| D634,630 S | 3/2011 | Taylor |
| D634,631 S | 3/2011 | Taylor |
| 7,959,597 B2 | 6/2011 | Baker et al. |
| D653,953 S | 2/2012 | Wakeman |
| D670,373 S | 11/2012 | Taylor et al. |
| 2002/0158089 A1* | 10/2002 | Mehta ........................... 222/420 |
| 2003/0062367 A1 | 4/2003 | Robinson et al. |
| 2005/0049620 A1 | 3/2005 | Chang |
| 2006/0253087 A1* | 11/2006 | Vlodaver et al. ............. 604/275 |
| 2008/0008979 A1 | 1/2008 | Thomas et al. |
| 2008/0294124 A1 | 11/2008 | Mehta |
| 2009/0234325 A1 | 9/2009 | Rozenberg et al. |
| 2009/0281454 A1 | 11/2009 | Baker et al. |
| 2011/0139149 A1 | 6/2011 | Cacka et al. |
| 2011/0139824 A1 | 6/2011 | Cacka et al. |
| 2011/0139826 A1 | 6/2011 | Hair et al. |
| 2011/0144588 A1 | 6/2011 | Taylor et al. |
| 2011/0184341 A1 | 7/2011 | Baker et al. |
| 2011/0319840 A1 | 12/2011 | Hair |

OTHER PUBLICATIONS

Author Unknown, "NasaFlo Neti Pot," http://www.neilmed.com/usa/nasaflo.php, 1 page, at least as early as Dec. 9, 2009.

Author Unknown, "SinuFlo Ready Rinse," http://www.neilmed.com/usa/sinuflo.php, 1 page, at least as early as Dec. 9, 2009.

Author Unknown, "Sinus Rinse Nasal Wash," http://www.neilmed.com/usa/sinusrinse.php, 3 pages, at least as early as Dec. 9, 2009.

Papsin et al., "Saline Nasal Irrigation," Canadian Family Physician, vol. 49, pp. 168-173, Feb. 2003.

Rabago et al., "Efficacy of Daily Hypertonic Saline Nasal Irrigation Among Patients with Sinusitus: A Randomized Controlled Trial," The Journal of Family Practice, vol. 51, No. 12, pp. 1049-1055, Dec. 2002.

Schumann et al., "Patients Insist on Antibiotics for Sinusitus? Here is a Good Reason to Say 'No'," The Journal of Family Practice, vol. 57, No. 7, pp. 464-468, Jul. 2008.

International Search Report, PCT/US2010/060901, 2 pages, Feb. 11, 2011.

* cited by examiner

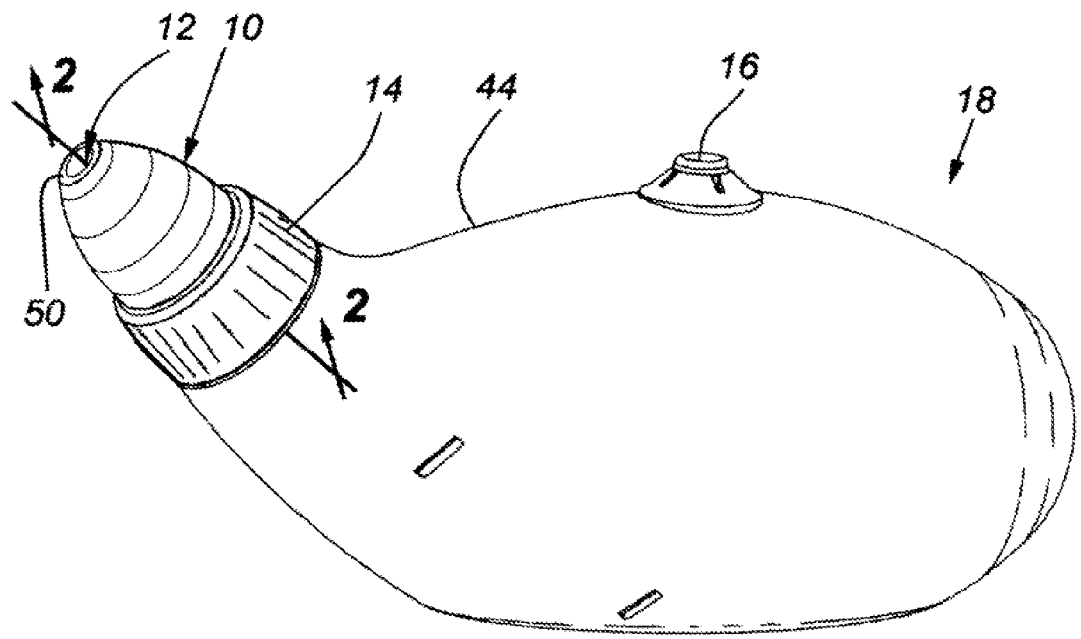
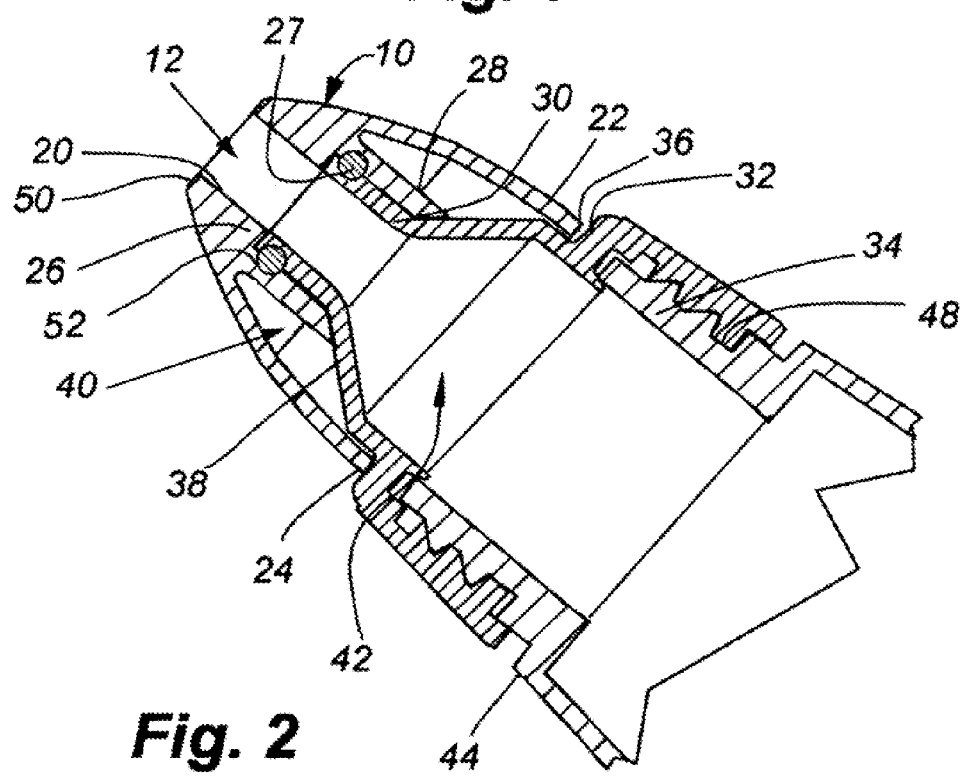

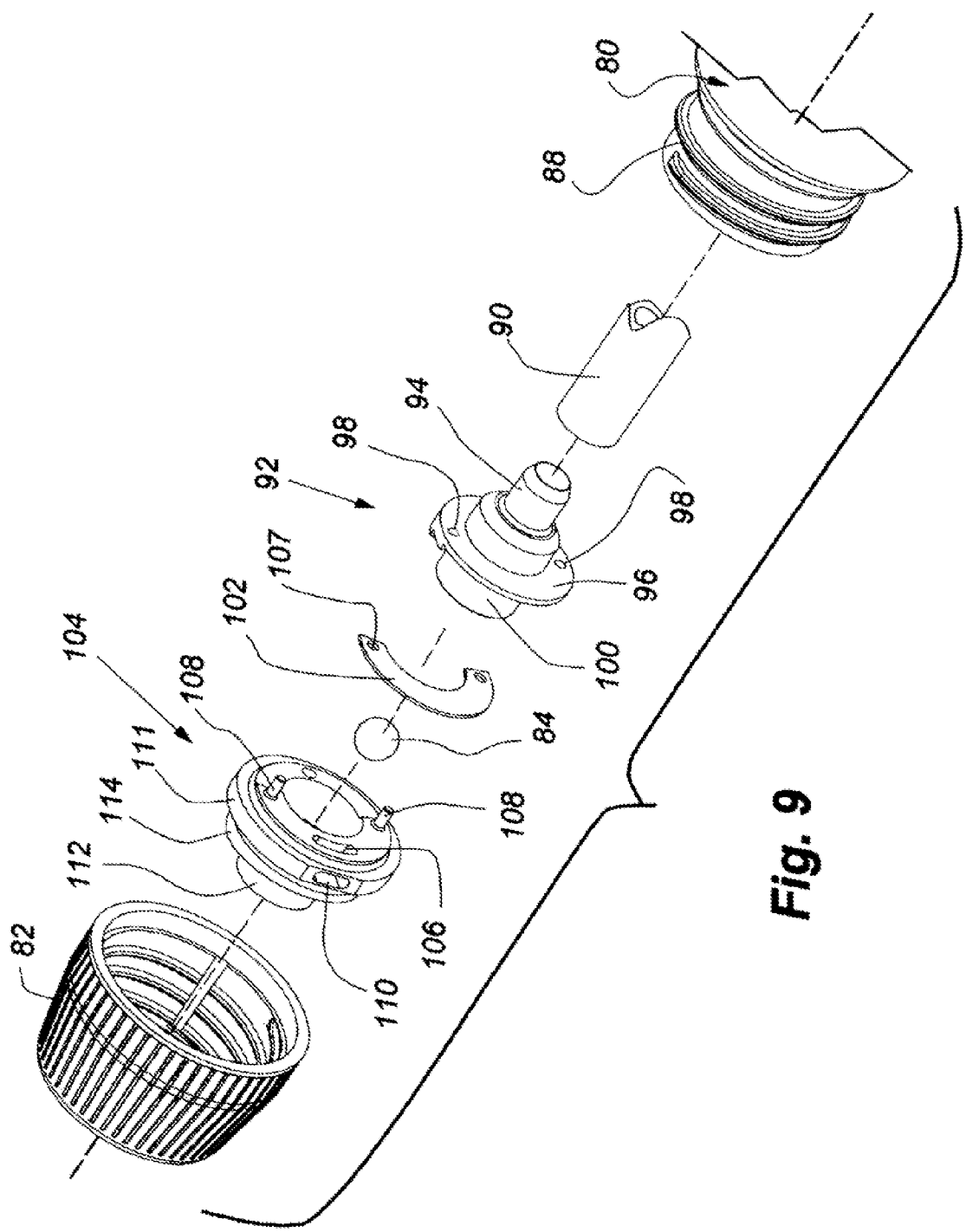

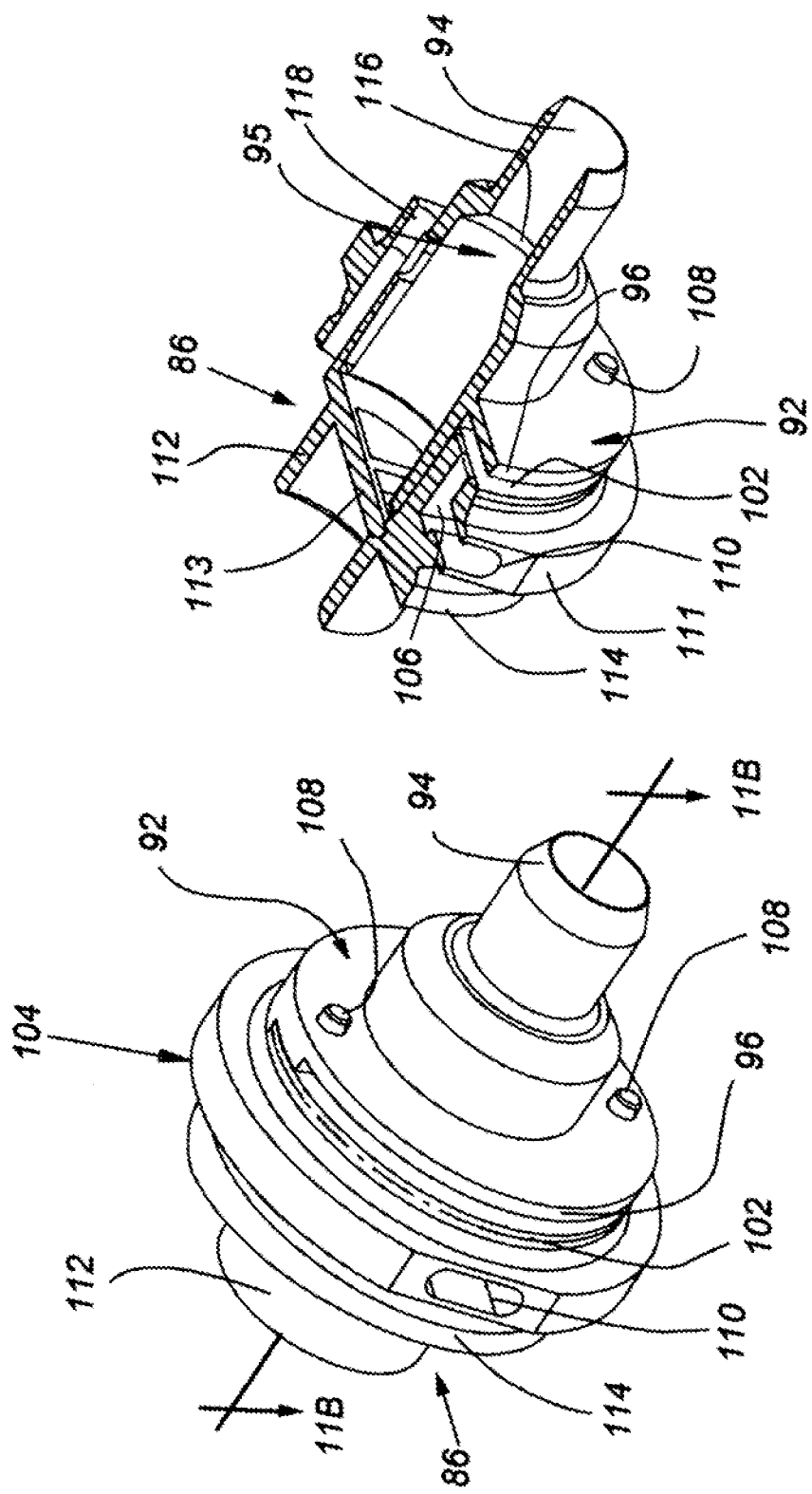

FACETED NASAL SEAL

CROSS-REFERENCE TO RELATED APPLICATIONS

This application is a divisional patent application of U.S. patent application Ser. No. 12/970,854, filed Dec. 16, 2010 and titled "Faceted Nasal Seal;" which is a continuation-in-part application claiming the benefit under 35 U.S.C. §120 of U.S. design application No. 29/364,669, entitled "Faceted Nasal Seal with Bottom Rim" and filed Jun. 25, 2010, U.S. design application No. 29/364,670, entitled "Faceted Nasal Seal" and filed Jun. 25, 2010, the disclosures of which are hereby incorporated by reference in their entireties. U.S. patent application Ser. No. 12/970,854 also claims the benefit under 35 U.S.C. §119(e) of U.S. provisional application No. 61/369,378, entitled "Faceted Nasal Seal" and filed Jul. 30, 2010, the disclosure of which is hereby incorporated by reference in its entirety.

This application is related to U.S. patent application Ser. No. 12/970,610, filed Dec. 16, 2010 and titled "Pot for Sinus Cavity Rinse," U.S. patent application Ser. No. 12/970,788, filed Dec. 16, 2010 and titled "Bottle for Sinus Cavity Rinse," U.S. patent application Ser. No. 12/970,345, filed Dec. 16, 2010 and titled "Powered Irrigator for Sinus Cavity Rinse" and U.S. patent application Ser. No. 12/970,415, filed Dec. 16, 2010 and titled "Squeeze Bottle for Sinus Cavity Rinse," the disclosures of which are herein incorporated by reference in their entireties.

FIELD

The present invention relates to fittings used to deposit sinus rinse solutions into a nasal cavity.

BACKGROUND

The benefits of rinsing one's sinus cavities have been well established, and include improving resistance to sinus infections, clogged sinuses, allergies, and general health. Oftentimes, however, the articles which one uses to rinse one's nasal passages make the process unnecessarily difficult and uncomfortable. One of the issues is related to the inability to obtain an effective seal between the nozzle of one of these articles and the user's nasal passage. If the seal is not adequate, during use the fluid can leak from between the nozzle and the nasal passage, thereby making the rinsing process messy.

In addition, the control of the flow from the vessel into the sinus cavity has not been adequate in the past, and users have found it difficult to regulate the volume of flow so as to make the rinsing process comfortable. In one existing product, as shown in U.S. Patent App. No. 2008/0294124, an aperture is formed in the lid of the vessel which can be used to restrict the flow of the fluid in the vessel through the nozzle during the rinsing step. However, because the aperture is positioned in the lid, the user uses one hand to hold the vessel and another hand to control the flow by covering and uncovering the aperture. This proves to be a relatively difficult process when the user is already in an awkward position, such as being positioned over a sink during the rinsing process.

It is to satisfy the above recognized issues that the present invention has been developed.

BRIEF SUMMARY

Certain embodiments take the form of a nozzle for a nasal rinse device including a collar that forms a conduit. The collar is configured to attach the nozzle to the nasal rinse device. An outlet aperture defined by the collar is on a top portion of the nozzle. The nozzle also includes a skirt extending outwards and downwards from the collar, and an outer surface of the skirt is partially faceted.

Other embodiments include a nasal rinse device having a body including a neck extending from a top portion of the body, and the body defines a cavity. The cavity holds a nasal rinse fluid. The nasal rinse device also includes an attachment collar configured to be secured to the neck. A nozzle is secured to the attachment collar. The nozzle includes a skirt having a faceted outer surface and an inner collar conduit defining an outlet aperture at an apex of the skirt. The inner collar conduit may be secured to the attachment collar. The inner collar extends downward from the skirt and is substantially surrounded by the skirt.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1 is an isometric view of a nozzle secured to a bottle for sinus rinse.

FIG. 2 is a cross-section view of the nozzle secured to the bottle viewed along line 2-2 in FIG. 1.

FIG. 9 is an exploded view of a valve housing, attachment collar and delivery tube connected to the squeeze bottle illustrated in FIG. 7.

FIG. 11A is an isometric view of the valve housing removed from the squeeze bottle.

FIG. 11B is a cross-section view of the valve housing viewed along line 11B-11B in FIG. 11A.

DETAILED DESCRIPTION

Figure 3A:
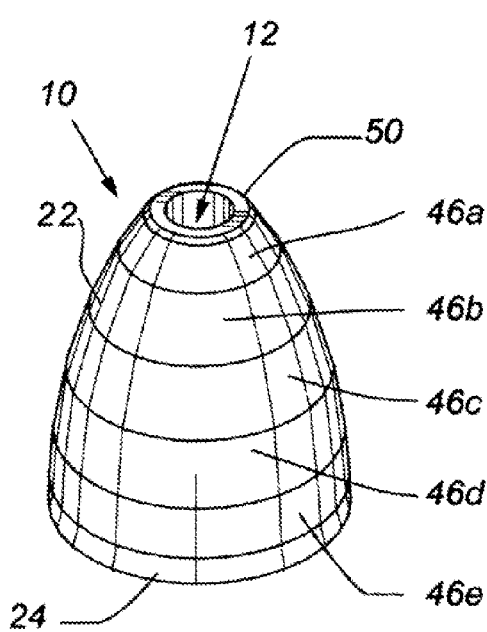
FIG. 3A is a top isometric of the nozzle illustrated in FIG. 1 removed from the bottle.

Several implementations of nozzles or fittings to be used with nasal rinse devices are disclosed herein. The nozzles may be attached to a variety of different nasal rinse apparatuses and create a seal between their outer surface and the user's nostril walls. The skirt or outer wall of the nozzles may be faceted or stepped. The faceted surface allows the nozzles to create a seal within the nasal cavity better than an oval or purely round nozzle. The skirt is generally rounded and includes an aperture located at its apex or tip. The aperture dispenses nasal rinse solution, e.g., a saline mixture, into the user's nostril.

In one embodiment, a tubular conduit or inner collar extends downwards from the aperture. The inner collar attaches to a corresponding conduit on the nasal rinse apparatus, creating a fluid passageway between the apparatus and the nozzle. The inner collar in some embodiments terminates before reaching the distal end of the nozzle. In these embodiments a portion of the nozzle may cover a portion of the nasal rinse apparatus, or cover a portion of the conduit fluidly connecting the nozzle and the nasal rinse device.

In some embodiments, the skirt terminates in an annular recessed groove formed around the circumference of the nozzle. In one embodiment, the recessed groove terminates and the nozzle expands into a shoulder or flange forming the bottom portion of the nozzle. In other embodiments, the body of the nozzle terminates at the end of the faceted skirt surface. However, in either embodiment the bottom area of the nozzle is open and covers a top area of the nasal rinse device.

When the nozzle is inserted into the user's nasal passage, the skirt or nozzle wall may compress radially inwards, conforming to the shape of the user's nasal passage. The terminal end of the skirt may engage a portion of the nasal rinse device, keeping that portion of the skirt from deflecting further inwardly, thus providing some structural rigidity to the flexion of the portion of the skirt extending between the tip and the terminal end of the nozzle. This provides some resistance to flexure to create a firm, but comfortable, fit of the nozzle within the user's nasal passage, and also facilitates the rebound of the skirt back to its original shape after being removed from the user's nasal passage.

FIG. 1 is an isometric view of a nasal rinse device 18 having a nozzle 10 attached to a reservoir body 44 of the nasal rinse device 18. FIG. 2 is a cross-section view of the nozzle 10 attached to the body 44. The nozzle 10 is attached to the body 44 via an attachment collar 14. The nasal rinse device 18 includes the reservoir body 44, which may be a squeeze bottle or a pour bottle and a vent 16, the nasal rinse device 18 is used to dispense nasal rinse solutions, for example, saline solution or solutions with other chemicals, into a user's nostril. In operation, the nozzle 10 is placed within the user's nostril and then the nasal solution stored within the reservoir body 44 may be poured or squeezed into the nostril. The vent 16 helps to prevent the fluid from pouring unevenly or bubbling out of the nozzle 10. The nozzle 10 creates a seal within the nostril to ensure the maximum amount of nasal solution is dispensed into the nostril without leaking around the sides of the nozzle 10.

Figure 3B:
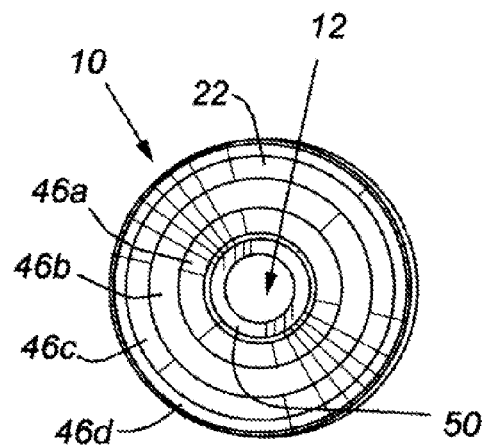
FIG. 3B is a top plan view of the nozzle.
Figure 3C:
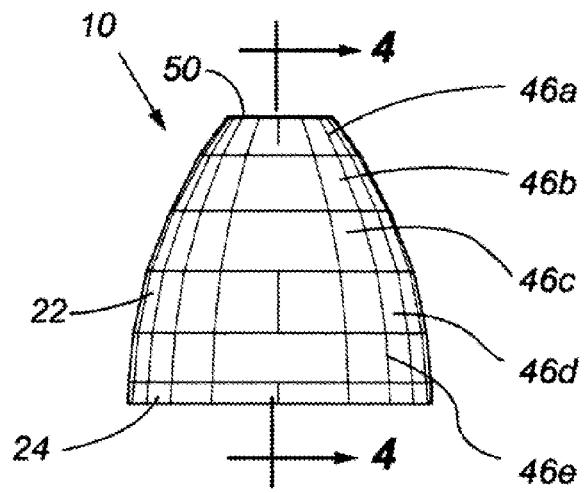
FIG. 3C is a side elevation view of the nozzle.
Figure 3D:
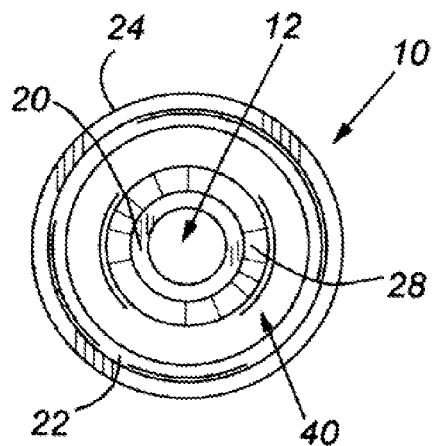
FIG. 3D is a bottom plan view of the nozzle.
Figure 3E:
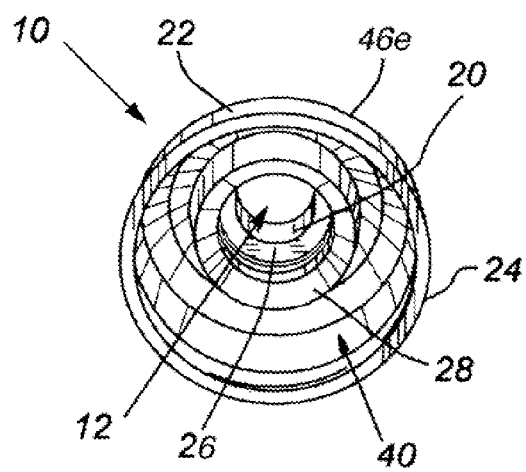
FIG. 3E is a bottom isometric view of the nozzle.
Figure 4:
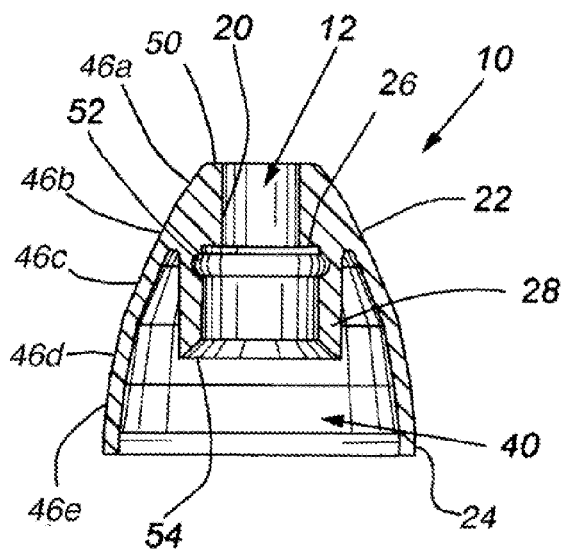
FIG. 4 is a cross is a cross-section view of the nozzle removed from the bottle, viewed along line 4-4 in FIG. 3C.

FIG. 3A is a top isometric view of the nozzle 10; FIG. 3B is a top plan view of the nozzle 10; FIG. 3C is a side elevation view of the nozzle 10; FIG. 3D is a bottom plan view of the nozzle 10; FIG. 3E is a bottom isometric view of the nozzle 10; and FIG. 4 is a cross-section view of the nozzle 10, as indicated by line 4-4 in FIG. 3C. Referring to FIGS. 3A-4, the nozzle 10 is self-sealing and is made of a soft elastomeric material, such as food grade silicone rubber. The nozzle 10 includes a tip 50 or apex which is the first portion of the nozzle 10 to enter the user's nostril when attached to the reservoir body 44. At a center portion of the tip 50 is an outlet aperture 12.

A skirt 22 or body is formed by a wall extending downwardly and away from the tip 50, as can be see from FIG. 3A, the skirt 22 is faceted or stepped circumferentially, or otherwise made up of regions having flat extensions or mixed flat and curved extensions, as the skirt 22 extends downwards. In some implementations the skirt 22 may have a wall thickness of approximately 0.040 inches.

The skirt 22 of the nozzle 10 acts to form a seal with the user's nostril when the nozzle 10 is attached to the reservoir body 44. The skirt 22 includes steps 46a-46e, which create ridges the outer surface of the skirt 22. In some implementations the steps 46a-46e may be approximately the same height; however each step 46a-46e may have a different average or center diameter. In these implementations, each step 46a-46e increases the overall outer diameter of the skirt 22 and the nozzle 10 maintains a generally rounded shape. For example, the first step 46a has a smaller average diameter than the second step 46b, and so on. In other implementations the steps 46a-46e may have different widths, such that the first step 46a may cover a greater portion of the outer surface of the skirt 22 than the second step 46b.

For example, as can been seen in FIG. 3A, the steps 46a-46e may be a series of stacked frustums having different outer wall angles. Each step 46a-46e is sloped at a predetermined angled and the outer wall has a larger diameter at the bottom edge of the steps 46a-46e than at the top edge of each step 46a-46e. In these implementations, each step 46a-46e decreases in diameter from the bottom edge to the top edge. Additionally, each step 46a-46e may have a different average diameter than the preceding step 46a-46e, this is because each step 46a-46e may have a different outer wall angle than the previous step 46a-46e. In some embodiments, the configuration of stacked frustum sections on top of one another may include ridges between each of the steps 46a-46e at the point of transition, from one step 46a-46e to the next, this gives the skirt 22 a faceted appearance and feel.

Figure 12:
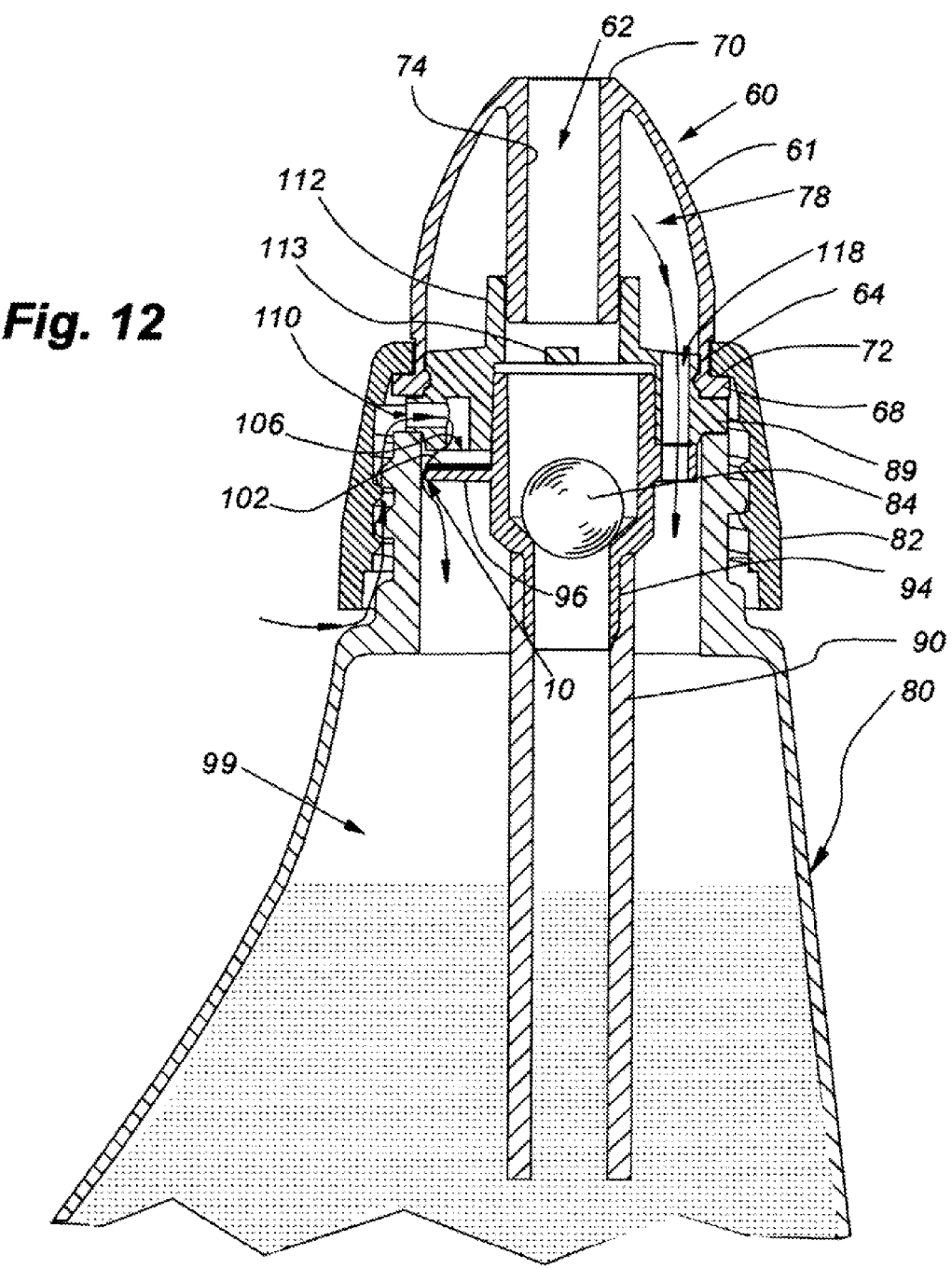
FIG. 12 is a cross-section view of the nozzle inserted into a user's nostril and connected to the squeeze bottle, viewed along line 12-12 in FIG. 7.

The tip 50 may be inserted into a user's nostril and one of the steps 46a-46e creates a seal between the nozzle 10 and the nostril walls (see FIG. 12). The particular step 46a-46e that engages the user's nostril depends upon the size of the user's nostril. For example, the larger the user's nostril the lower the step 46a-46e may be that engages the nostril wall. The steps 46a-46e create a better seal than a purely rounded nozzle, as the steps 46a-46e better conform to the nostril wall—the nostril wall is not purely oval-shaped or conical-shaped—and the steps 46a-46e better mimic the inner surface of the nostril wall. It should be noted that although five steps 46a-46e have been illustrated, any number of steps 46a-46e may be included. The number of steps 46a-46e may be altered to create a smoother or rougher skirt 22. For example, depending on the desired sealing level the number of steps 46a-46e may be increased or decreased.

The skirt 22 terminates at a terminal edge 24. In some embodiments the terminal edge 24 may be a continuation of the steps 46a-46e and in other embodiments the terminal edge 24 may extend past the steps 46a-46e creating a shoulder, flange, or the like (see, e.g., the embodiment of FIGS.

3A-3E). In these embodiments, the nozzle 10 may be substantially free-standing along the skirt 22, i.e., the skirt 22 and/or other outer surfaces of the nozzle 10 may be substantially unrestricted. As can be seen from FIG. 2, the terminal edge 24 is unrestricted by the attachment collar 14.

Referring now to FIGS. 2 and 4, the nozzle 10 has an inner collar 28 creating a conduit or passageway within the inner surface of the nozzle 10. The inner collar 28 may be formed integrally with the skirt 22. The inner collar 28 may be substantially hollow and terminate at the tip 50 creating the outlet aperture 12. The distal end of the inner collar 28 terminates inside the skirt 22. In some implementations the inner collar 28 may extend as far as the terminal edge 24 of the skirt 22 and in other implementations (such as the implementation illustrated in FIGS. 2 and 4) the inner collar 28 may have a terminal edge 54 that is beveled and terminates at a point above the terminal edge 24 of the skirt 22. The wall thickness of the inner collar 28 in some embodiments may be approximately 0.060 inches.

The inner collar 28 extends downward from the outlet aperture 12 and may mate and fluidly connect with the end portion 42 of the outer collar 14 along the outlet conduit 30, attaching the nozzle 10 to the reservoir body 44. The inner collar 28 may include an annular recess 52 along its inner walls to receive an o-ring or other sealing mechanism. The tip 50 of the nozzle 10 above the annular recess 52 extends down to a cylindrical wall 20 that defines the outlet aperture 12, and the tip 50 may be thicker than the wall of the inner collar 28, the inner collar 28 thus may have a larger inner diameter than the cylindrical wall 20 forming the outlet aperture 12. A shoulder 26 formed in the tip 50 of the nozzle 10 may be formed around the aperture 12 and engage with the end of the outlet conduit 30.

As can be seen from FIG. 2, the inner collar 28 connects with the outlet conduit 30 of the outer collar 14. The outlet conduit 30 extends from an end portion 42 of the collar 14. The outer collar 14 is secured to the reservoir body 44 of the nasal rinse device 18 via collar threading 48 and complementary bottle threading 34, or the like. The nozzle 10 may be attached to the outer collar 14 before or after the outer collar 14 is attached to the reservoir body 44. The nozzle 10 is placed above the outlet conduit 30 and the outlet conduit 30 may be inserted partially into the inner collar 28. In some implementations the outlet conduit 30 may extend only partially into the inner collar 28. Furthermore, an o-ring 27 may be secured within the annular recess 52 to create a fluid-tight seal between the inner collar 28 and the outlet conduit 30.

The skirt 22 extends away from the outlet aperture 12 and thus extends away from the outlet conduit 30 creating a void 40 or open space between a diameter reduction neck 38 of the end portion 42 of the outer collar 14 and the skirt 22. The void 40 or annular spacing is formed between the skirt 22 and the inner collar 28, and the wall forming the skirt 22 extends further from the tip 50 than does the wall forming the inner collar 28 such that the terminal edge 24 of the skirt 22 is positioned around a shoulder 32 of the end portion 42 of the outer collar 14. The void space 40 may be annular and may be continuous or discontinuous within the skirt wall.

The terminal edge 24 of the skirt 22, as well as the adjacent wall structure of the skirt 22, may closely fit with outer collar 14, but not necessarily engage the outer collar 14. Also, a small gap 36 may be formed between the shoulder 32 and the terminal edge 24 of the skirt 22. As discussed above, the terminal edge 24 of the skirt 22 may not attach to or otherwise be affixed to the outer collar 14 and may move relative thereto. In other implementations the skirt 22 may rest along the outer collar 14 or otherwise contact the outer collar 14.

In these implementations, the user inserts the tip 50 into a user's nostril and then tips the reservoir body 44, allowing the nasal solution to travel from the reservoir body 44 to the outlet conduit 30. However, in some instances, the reservoir body 44 may be flexible or squeezable, and the user may squeeze the reservoir body 44 to force solution to travel from the reservoir body 44 to the outlet conduit 30. Once the nasal solution enters the outlet conduit 30, the solution enters the inner collar 28 and exits into the nasal cavity via the outlet aperture 12. As the nozzle 10 creates a seal between the nostril wall and the skirt 22 via the facets or steps 46a-46e, the nasal solution is deposited into the nasal cavity without substantially leaking around the nozzle 10 and the user's nostril.

The skirt 22, when positioned in the user's nasal passage, flexes inwardly into the void 40 formed as the skirt 22 extends away from the connection between the nozzle 10 and the outlet conduit 30. As the skirt 22 flexes when sealing with the user's nostril, it may do so radially and/or irregularly around its circumference in order to closely match the shape of the user's nostril. This helps create an adequate seal between the user's nostril and the nozzle 10 structure. When the nozzle 10 is removed from the user's nostril, the elastomeric material of the skirt 22 springs back into its original shape. Additionally, the gently curving, cone-like shape of the nozzle 10 from the tip 50 down to the terminal edge 24 of the skirt 22 allows for a close fit with a variety of sizes of nasal passages.

Figure 5A:
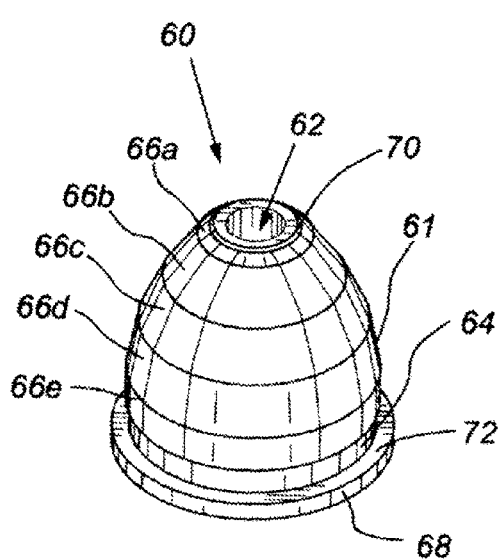
FIG. 5A an isometric view of another embodiment of a nozzle.
Figure 5B:
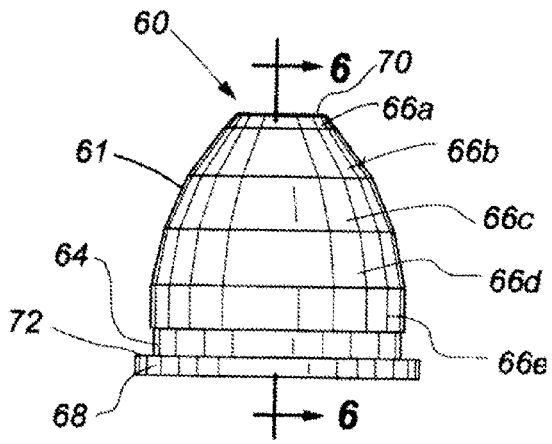
FIG. 5B is a side elevation view of the nozzle illustrated in FIG. 5A.
Figure 5C:
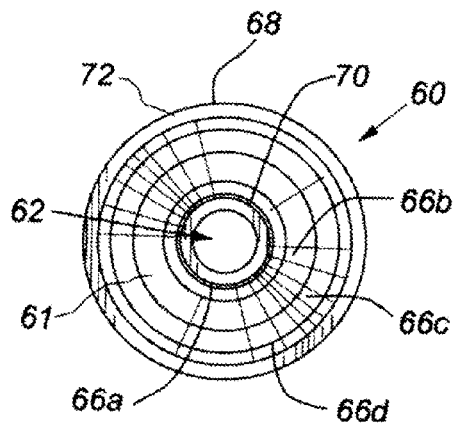
FIG. 5C is a top plan view of the nozzle illustrated in FIG. 5A.
Figure 5D:
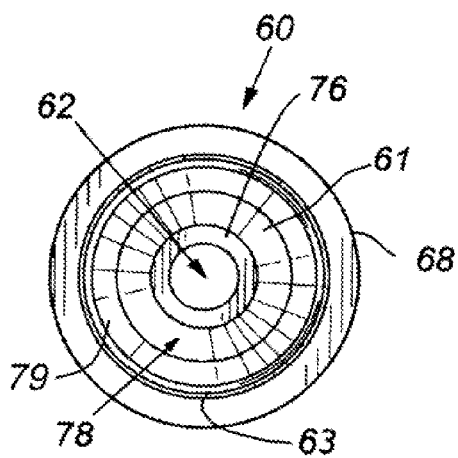
FIG. 5D is a bottom plan view of the nozzle illustrated in FIG. 5A.
Figure 5E:
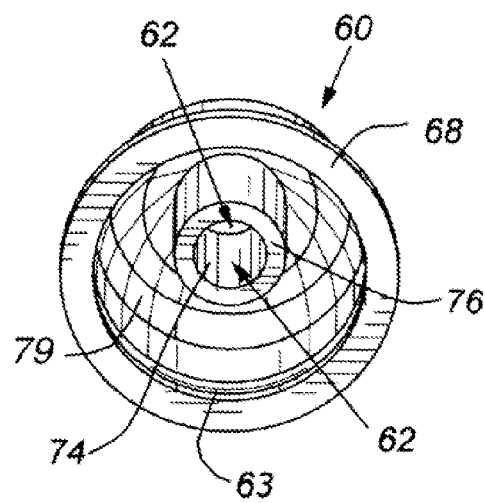
FIG. 5E is a bottom isometric view of the nozzle illustrated in FIG. 5A.
Figure 6:
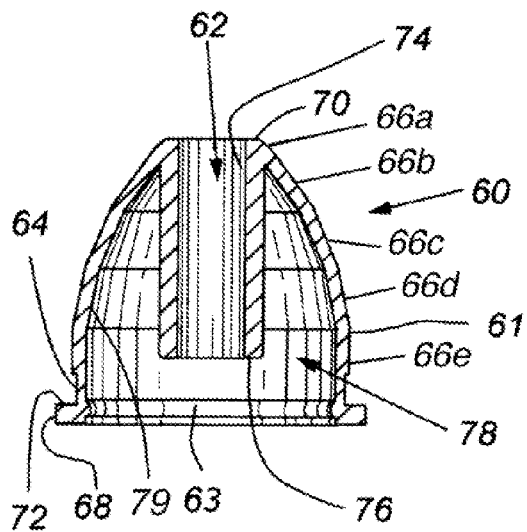
FIG. 6 is a cross-section view of the nozzle illustrated in FIG. 5A, viewed along line 6-6 in FIG. 5B.

FIGS. 5A-5E illustrate another embodiment of a nozzle. In this embodiment the nozzle 60 may include a flange 68 at the terminal edge 24 of the skirt 61. Additionally, the skirt 61 in this embodiment defines at a recessed groove 64, which then expands outwards forming the flange 68. FIG. 5B illustrates an side elevation view of the nozzle 60 and FIG. 5C is a top plan view of the nozzle 60. Referring to FIGS. 5A-6, the nozzle 60 includes an outlet aperture 62 located at the apex of the tip 70. Extending outward and downward from the outlet aperture 62 is the skirt 61. The skirt 61, similar to the skirt 22 illustrated in FIGS. 3A-3E, includes steps 66a-66e or facets along its outer surface. The steps 66a-66e also act to provide a seal against a nostril wall when the nozzle 60 is inserted into a user's nasal cavity. In this implementation, the skirt 61 may include a larger diameter at its open bottom as compared with the nozzle 10 illustrated in FIGS. 3A-3E. However, in other embodiments the nozzles 10, 60 may include similar sized diameters.

The skirt 61 illustrated in FIGS. 5A-6 terminates at the recessed groove 64, which has a smaller diameter than the fifth step 66e, such that the diameter of the nozzle 60 decreases after the fifth step 66e. The recessed groove 64 then expands into the flange 68, which has a larger diameter than the fifth step 66e. In this implementation, the groove 64 reduces the diameter of the nozzle 60 at the end of the skirt 61. The groove 64 may be used to better attach the nozzle 60 to a nasal rinse reservoir by providing a connection location. In other embodiments the groove 64 may be used to reduce the material used to create the nozzle 60. As can been seen from FIG. 5C, the flange 68 may form the largest diameter of the nozzle 60 and may be larger than any of the steps 66a-66e. The recessed groove 64 and the flange 68 may be used to secure the nozzle 60 to a nasal rinse squeeze bottle, which will be discussed in more detail below with respect to FIGS. 7 and 8. An annular bead 63 is formed on the inner diameter of the lower end of the skirt wall 61 for receipt in an annular groove 114 formed on the outer periphery of the upper check valve housing 104.

Referring now to FIGS. 5A-6, the nozzle 60 includes an inner collar 74 or conduit extending downwards from the tip 70, creating the outlet aperture 62. The inner collar 74 may be similar to the inner collar 28 illustrated in FIG. 6, however, in this implementation the inner collar 74 may extend to the tip 70 and be substantially the same diameter throughout its entire length. The inner collar 74 extends downward and is surrounded by the skirt 61. The distal end 76 of the inner collar 74 terminates before extending as far as the outer groove 64 or the flange 68. However, in other embodiments the inner collar 74 may extend the entire length of the nozzle 60. In some implementations, the inner collar 74 may have a wall thickness of approximately 0.060 inches.

As can be seen in FIGS. 5A-6, the inner wall 79 of the skirt 61 surrounds the inner collar 74 and the inner collar 74 is separated from the inner wall 79, such that the inner collar 74 and the inner wall 79 may not contact each other. In this implementation, the space between the inner collar 74 and the inner wall 79 of the skirt 61 creates a void 78 or empty area when the nozzle is connected to the squeeze bottle reservoir 99.

Figure 7:
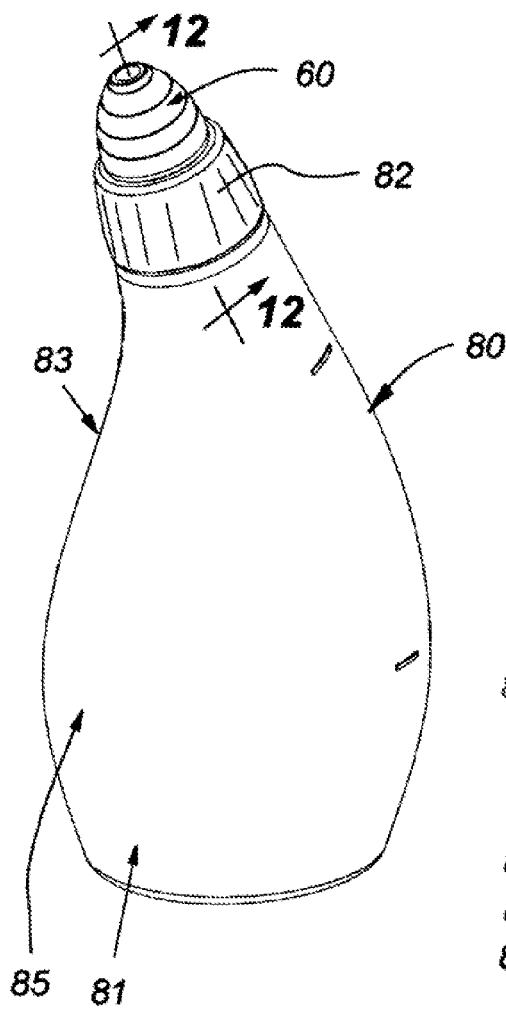
FIG. 7 is an isometric view of the nozzle illustrated in FIG. 6 secured to a squeeze bottle.
Figure 8:
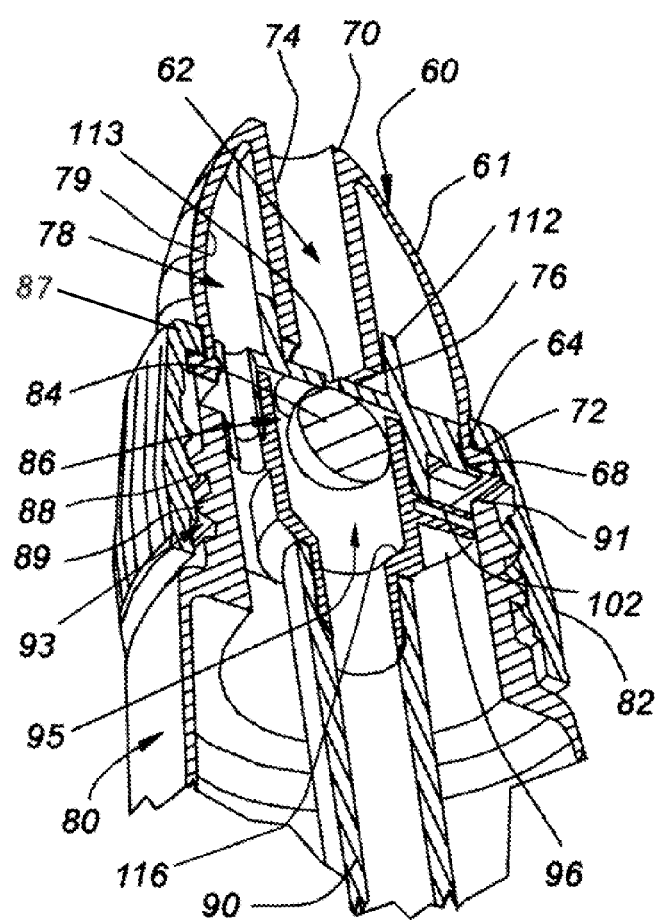
FIG. 8 is a cross-section view of the nozzle secured to the squeeze bottle viewed along line 8-8 in FIG. 7.

FIGS. 7 and 8 illustrate the second nozzle 60 embodiment attached to a nasal rinse squeeze bottle 80. The squeeze bottle 80 includes a main body 85 that may be made of low density polyethylene (LDPE). The main body 85 defines a reservoir in which a solution is placed for use in rinsing a user's nasal cavity. A top portion 83 of the main body 85 includes an opening upon which the nozzle 60 may be secured. The nozzle 60 is secured to the main body 85 by an attachment collar 82.

The attachment collar 82 is similar to the attachment collar 14 illustrated in FIG. 1. However, in this implementation the attachment collar 82 extends over a portion of the nozzle 60, to better secure the nozzle 60 to the squeeze bottle 80. The outer diameter of the nozzle 60 at the flange 68 may be less than the outer diameter of the attachment collar 82 holding the nozzle 60 to the squeeze bottle 80. The attachment collar 82 may have a sloped outer surface angling from a smaller diameter to a larger diameter in the direction from top to bottom to form an annular frustum. An inner wall of the attachment collar 82 may define threads 89 for engagement with the squeeze bottle 80. A bottom portion of the attachment collar 82 may have a vertical sidewall.

A top shelf or shoulder 87 of the attachment collar 82 sits on top of the flange 68 and rests on the upper surface 72 of the flange 68. The shoulder 87 of the attachment collar 82 may have a smaller inner diameter than the outer diameter of the flange 68 of the nozzle. Additionally, the shoulder 87 extends at least partially into the recessed groove 64 on the nozzle 60. The shoulder 87 may have an inner diameter similar to the outer diameter of the recessed groove 64. The attachment collar 82 helps anchor the nozzle 60 as well as create an airtight seal when the nozzle 60 is held in place against the squeeze bottle 80.

The outlet aperture 62 allows the solution inside the main body reservoir 99 to exit the squeeze bottle 80 as desired by the user. The main body 85 has a lower portion 81, which is relatively bulbous and fits well in a user's hand, and a top portion 83 which narrows down significantly from the bottom portion 81 to a generally circular dimension having an outer maximum dimension approximately the same as the maximum dimension of the attachment collar 82.

The nozzle 60 may be held to the top of the squeeze bottle 80 by the attachment collar 82. Additionally the flange 68 is retained against a collar of a check valve 86 (further described below), which in turn is retained against a top rim 91 of the main body 85 of the squeeze bottle 80. Each of these is retained in position by the shoulder 87 of the attachment collar 82, which once positioned over the nozzle 60 and threadedly engaged with the threads 88 on the outer perimeter of the top portion 83 of the main body 85, clamps the flange 68 of the nozzle 60 and the check valve 86 to the top of the squeeze bottle 80.

The nozzle 60 is also attached to the check valve 86 by the inner collar 74. The valve assembly 86 includes an upwardly extending rim 112 that connects with the inner collar 74, fluidly connecting the inside of the squeeze bottle 80 with the outlet aperture 62 of the nozzle 60. In this implementation the inner collar 74 may be received partially within the extending rim 112. However, in other embodiments, the extending rim 112 may be received within the inner collar 74, similar to the connection between the outlet conduit 30 and the inner collar 28 illustrated in FIG. 2. Additionally, an o-ring or other sealing mechanism may be inserted within the rim 112 to fit around the inner collar 74 in order to better seal the connection between the extending rim 112 and the inner collar 74.

Figure 10A:
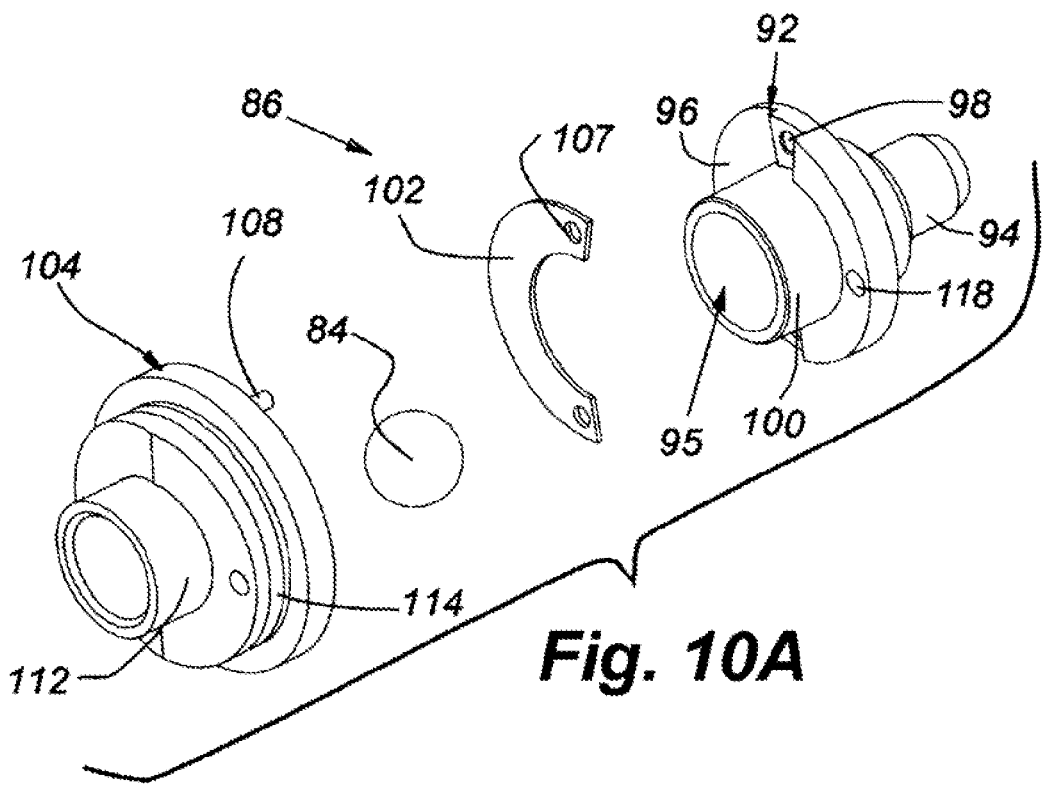
FIG. 10A is an enlarged, left-side, exploded isometric view of the valve housing illustrated in FIG. 9.
Figure 10B:
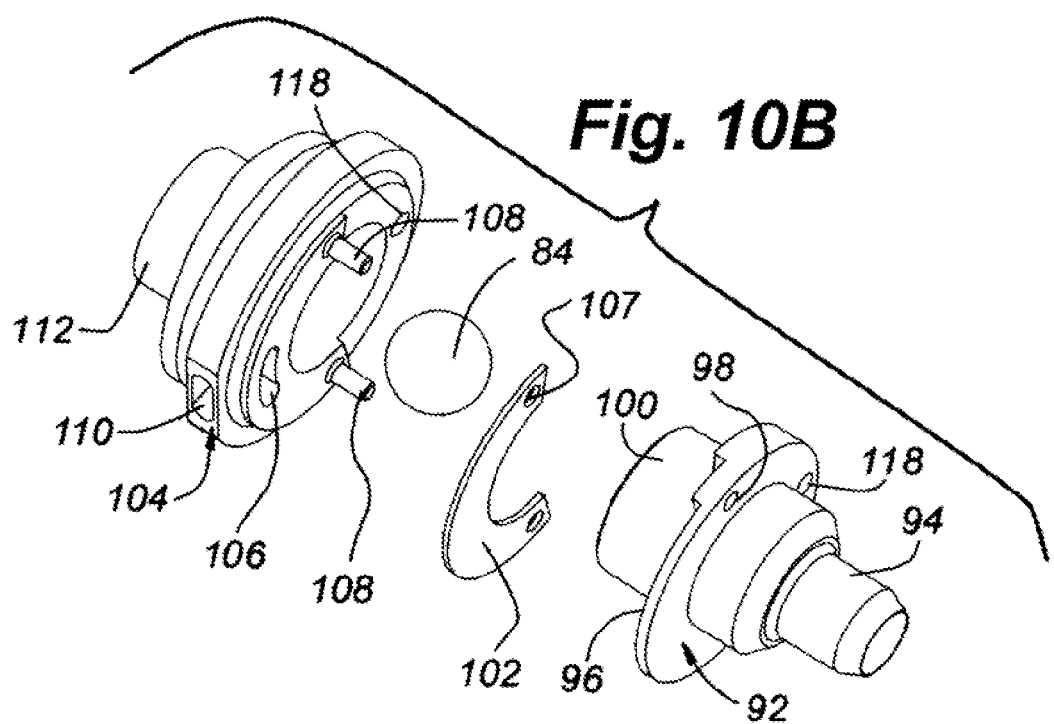
FIG. 10B is an enlarged, right-side, exploded isometric view of the valve housing illustrated in FIG. 9.
Figure 13:
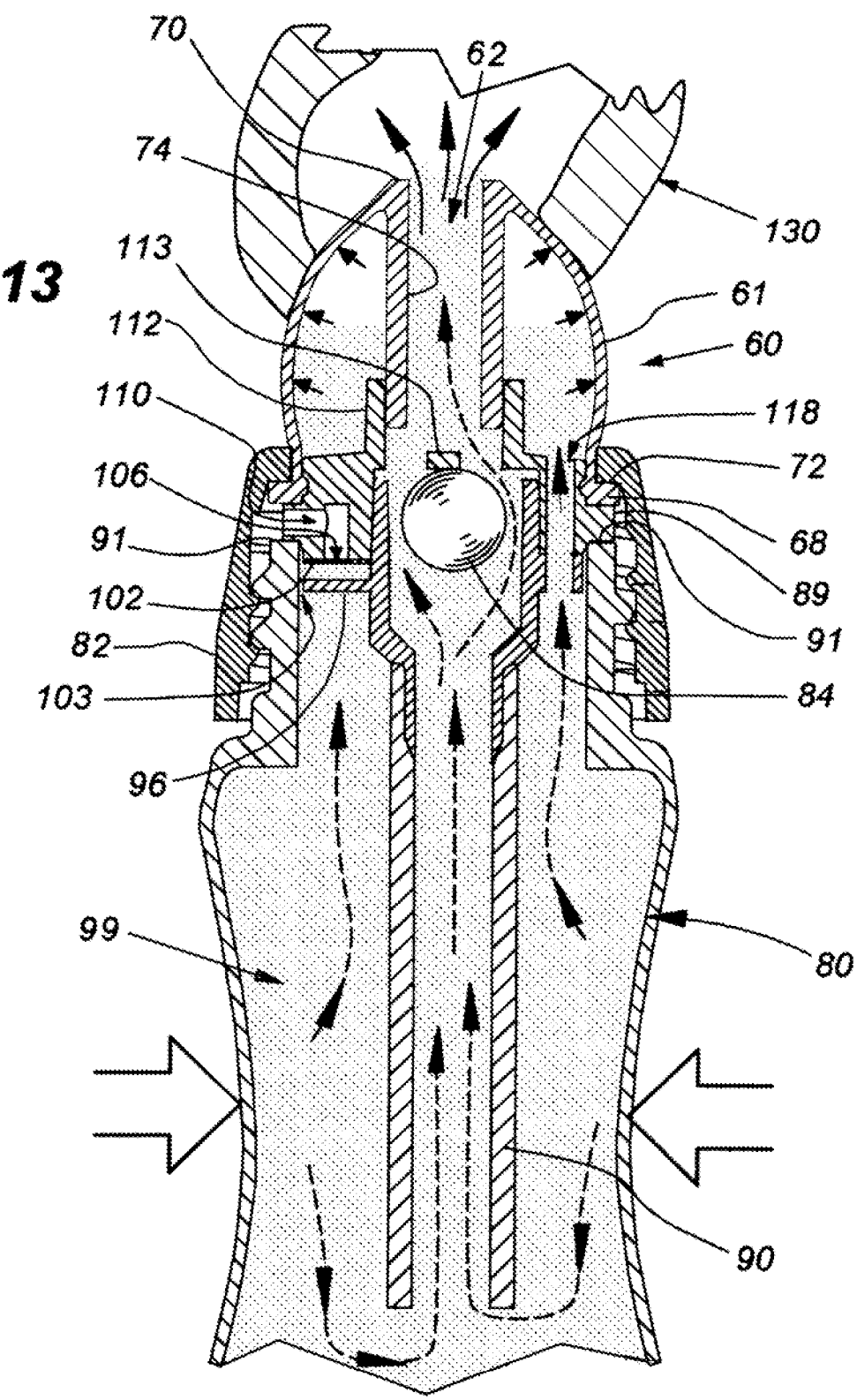
FIG. 13 is a cross-section view of the nozzle inserted into a user's nostril and dispensing fluid therein.

FIG. 8 illustrates a cross-section view of the nozzle 60 secured to the squeeze bottle 80 and FIG. 9 illustrates an exploded view of the attachment collar 82 and the check valve 86. FIG. 10A is an enlarged, left-side, exploded isometric view of the valve housing illustrated in FIG. 9. FIG. 10B is an enlarged, right-side, exploded isometric view of the valve housing illustrated in FIG. 9. FIG. 11A is an isometric view of the valve housing removed from the squeeze bottle. FIG. 11B is a cross-section view of the valve housing viewed along line 11B-11B in FIG. 11A. Referring to FIGS. 8, 12 and 13, the check valve 86 is positioned in fluid communication between the outlet aperture 62 in the nozzle 60 and a delivery tube 90 extending from the bottom of the check valve 86 into the reservoir formed in the squeeze bottle 80. The check valve 86 has an upper portion 104 and a lower portion 92, as shown in FIG. 9, and defines a contained space forming a cavity 95.

Referring to FIGS. 9-11B, the upper portion 104 and the lower portion 92 of the check valve 86 may be secured together via attachment pegs 108 extending from a bottom surface of the upper portion 104. The attachment pegs 108 are received within receiving apertures 98 on the lower portion 92 of the housing. The attachment pegs 108 may also attach to a reed valve 102 through securing apertures 107 disposed on the reed valve 102. In this implementation, the upper housing 104, the reed valve 102, and the lower housing 92 are secured together to form the check valve 86 as illustrated in FIG. 11A.

The delivery tube 90 is attached to an annular extension 94 extending from the bottom of the check valve 86. The delivery tube 90 fluidly connects liquid within the reservoir 99 of the squeeze bottle 80 to the check valve 86. The bottom end of the inner collar of the nozzle 60 is fluidly connected to the extending rim 112 formed from the top of the check valve 86. A nipple extension 94 extends from the bottom of the lower portion 92 of the check valve 86 for receiving the top end of the liquid delivery tube 90 in a friction fit engagement. The end of the nipple extension 94 may be chamfered to help guide the liquid delivery tube 90 onto the nipple extension 94.

Referring to FIGS. 8, 10A, and 11B, a cavity 95 is formed within the lower portion 92, and a valve seat 116 is formed near the bottom of the cavity 95 by a circular conical wall. A retention structure 113 is formed within the upper portion 104 to cap the top of the cavity 95. The retention structure 113 allows fluid through but does not allow a ball member 84 through. The retention structure 113 is disposed between the extending rim 112 and the cavity 95 in the lower portion 92 of the check valve 86 when the upper portion 104 and the lower portion 92 are connected together. The extending rim 112 is fluidly connected to the outlet aperture 62 when the nozzle 60 is connected to the squeeze bottle 80. The cavity 95 acts as a fluid conduit, connecting the delivery tube 90 and the extending rim 112. Additionally, the sidewalls of the cavity 95 are generally cylindrical, and taper at their bottom ends to form the valve seat 116.

The ball 84 may move freely within the cavity 95. However, the retention structure 113 is at the top of the cavity 95. The retention structure 113, which may be in the shape of a cross extending across the fluid passageway formed through the center of the check valve 86, prevents the ball 84 from moving out of the cavity 95 into the upper portion 104 of the check valve 86. The cavity 95 and the retention structure 113 are in fluid communication with the inner collar 74 above and the liquid delivery tube 90 extending below into the squeeze bottle 80. When the ball 84 is on the valve seat 116, the fluid in the cavity 95 above the ball 84 is largely restricted from flowing back down into the liquid delivery tube 90, and thus may not go back into the squeeze bottle 80. In this way, any liquid coming back into the nozzle 60 is unlikely to contaminate the liquid in the squeeze bottle 80.

As shown in FIG. 11B, the check valve 86 also defines a passageway 118 creating communication for air or liquid from the reservoir 99 of the squeeze bottle 80 through the passageway 118 and into the void space 78 between the nozzle 60 and the check valve 86. The passageway 118 has a lower opening into the squeeze bottle 80 and an upper opening into the void space 78.

As shown in FIGS. 11A, 11B, and 12, the inlet port 106 is formed in the check valve 86 that communicates between the reservoir 99 of the squeeze bottle 80 and the atmosphere. The threading 89 of the attachment collar 82 and the threading 88 of the squeeze bottle 80 are designed to create a void 93 to allow an air gap between adjacent threads. Thus, air can travel in a spiral path between the threads 88, 89 to enter the inlet port 106 and fill the reservoir in the squeeze bottle 80 after fluid has been dispensed, thus preventing the check valve 86 from creating a vacuum.

Referring to FIGS. 11A, 11B, 12 and 13 the reed valve 102 is disposed between the upper portion 104 and lower portion 92 of the check valve 86. The reed valve 102 covers the air inflation port 110 to selectively connect the inlet port 106 to the reservoir 99 of the squeeze bottle 80. The inlet port 106 is the internal opening of the air inflation port 110. The reed valve 102 may be a flat flexible semi-circular plate structure which is attached on the pegs 108 between the upper portion 104 and the lower portion 92 at its ends in a cantilever fashion. This reed valve 102 is typically in a closed position and opens under the negative pressure of the squeeze bottle 80 when moving from a squeezed to the un-squeezed position. The reed valve 102 material may be FDA grade silicone rubber and may be approximately 0.015 inches thick. A guard plate 96 extends radially outwardly from the outer surface of the lower portion 92 of the check valve 86 in order to protect the reed valve 102 from interference by particulates and also to keep the reed valve 102 from opening too far. A small gap 103 is formed between the end of the guard 96 and the inner wall of the top portion 104 of the main body 85 to allow air or liquid to flow therethrough towards the reed valve 102 and the inflation port 110.

Referring to FIGS. 12 and 13, in operation, with fluid pressure from below when the squeeze bottle 80 is squeezed, the fluid travels via the delivery tube 90 and pushes the ball 84 out of the valve seat 116 up against the retention structure 113. Liquid then flows around the ball 84 and the retention structure 113 and out the outlet aperture 62 of the nozzle 60.

The passageway 118 formed through the check valve 86 allows air or liquid pressure to be applied to the skirt 61 walls when the squeeze bottle 80 is squeezed. The liquid cannot escape through the inflation port 110 because of the reed valve 102 is closed.

When the nozzle 60 is inserted into the user's nostril opening 130, the skirt 61 may deform based on contact with the edges of the nostril. When the squeeze bottle 80 is squeezed, the pressure increases from liquid or air pressure inside the void space 78 in the nozzle 60, thus creating an outward pressure on the skirt 61 walls of the nozzle 60 and enhancing the fit of the nozzle 60 within the nostril of the user. When the squeeze bottle 80 is not being squeezed, the squeeze bottle 80 is resilient and returns to its original shape relieving the pressure of the fluid or nasal solution on the ball 84, allowing the ball 84 to move back down into the valve seat 116 prevents fluid from flowing back into the reservoir 99. This is beneficial as it prevents fluid that may come back into the outlet aperture 62 from the user's nostrils or sinus from draining into the reservoir in the squeeze bottle 80.

Furthermore, the inlet port 106 in combination with the reed valve 102 substantially prevent a vacuum from occurring within the squeeze bottle 80 after squeezing. After squeezing, the squeeze bottle 80 reservoir 99 may be under negative pressure and the reed valve 102 opens based on this pressure. When the reed valve 102 opens, the inlet port 106 connects to the reservoir 99, as the inflation port 110 becomes unblocked, allowing air to enter into the reservoir 99 of the squeeze bottle 80 to re-inflate the squeeze bottle 80. After the squeeze bottle 80 has returned to its original shape and pressure within the reservoir 99 has been equalized, the reed valve 102 returns to the closed position. This helps to prevent the squeeze bottle 80 from remaining in a compressed shape after the user has stopped squeezing the bottle 80.

A variety of embodiments and variations of structures and methods are disclosed herein. Where appropriate, common reference numbers were used for common structural and method features. However, unique reference numbers were sometimes used for similar or the same structural or method elements for descriptive purposes. As such, the use of common or different reference numbers for similar or the same structural or method elements is not intended to imply a similarity or difference beyond that described herein.

While the methods disclosed herein have been described and shown with reference to particular steps performed in a particular order, it will be understood that these steps may be combined, subdivided, or re ordered to form an equivalent method without departing from the teachings of the present invention. Accordingly, unless specifically indicated herein, the order and grouping of the steps are not generally intended to be a limitation of the present invention.

The references herein to "up" or "top", "bottom" or "down", "lateral" or "side", and "horizontal" and "vertical", as well as any other relative position descriptor are given by way of example for the particular embodiment described and not as a requirement or limitation of the vessel or the apparatus and method for assembling the vessel. Reference herein to "is", "are", "should", "would", or other words implying a directive or positive requirement are intended to be inclusive of the permissive use, such as "may", "might", "could" unless specifically indicated otherwise.

The apparatus and associated method in accordance with the present invention has been described with reference to particular embodiments thereof. Therefore, the above description is by way of illustration and not by way of limitation. Accordingly, it is intended that all such alterations and variations and modifications of the embodiments are within the scope of the present invention as defined by the appended claims.

What is claimed is:

1. A nozzle comprising
a collar forming a conduit, wherein the collar is configured to attach to a reservoir conduit within a reservoir;
an outlet aperture defined within a tip of the nozzle; and
a skirt extending downwards from the tip, wherein an outer surface of the skirt comprises a plurality of facets wherein each facet of the plurality of facets defines a frustum surface extending outward from a center axis of the nozzle at an angle with respect to the center axis of the nozzle and the angle for each successive facet downward from the tip is larger than the angle of each previous facet.

2. The nozzle of claim 1, wherein the plurality of facets comprises
a first frustum defining a first frustum surface;
a second frustum defining a second frustum surface positioned on top of the first frustum;
a third frustum defining a third frustum surface positioned on top of the second frustum;
a first inflection point defined at an intersection between the first frustum and the second frustum; and
a second inflection point defined at an intersection between the second frustum and the third frustum; wherein
the first frustum has a first tangent that includes atop edge of the frustum and the first inflection point and intersects with a center axis of the nozzle to form a first angle;
the second frustum has a second tangent that includes the first inflection point and the second inflection point and intersects with a center axis of the nozzle to form a second angle;
the third frustum has a third tangent that includes the second inflection point and a bottom edge of the third frustum and intersects with a center axis of the nozzle to form a third angle;
the first angle is larger than the second angle; and
the second angle is larger than the third angle.

3. The nozzle of claim 1, wherein the collar is substantially surrounded by the skirt.

4. The nozzle of claim 1, wherein the outlet aperture is fluidly connected to the conduit in the collar.

5. The nozzle of claim 1 further comprising an annular space between the collar and the skirt, wherein in a first position the skirt does not substantially contact the collar.

6. The nozzle of claim 1 further comprising an annular recess formed in a distal end of the collar, wherein the annular recess is configured to receive an O-ring.

7. The nozzle of claim 1, wherein the outer surface of the skirt is substantially convex from the tip to an edge of the skirt.

8. The nozzle of claim 1, wherein
the collar is cylindrically shaped and includes a terminal edge, wherein the terminal edge of the collar defines a beveled edge; and
a terminal edge of the skirt extends further than a terminal edge of the collar.

9. The nozzle of claim 1 further comprising a shoulder positioned between the collar and the tip, wherein the shoulder reduces a diameter of a flow pathway defined between the collar and the outlet aperture.

10. The nozzle of claim 1, further comprising an annular bead formed on an inner surface of a bottom end of the skirt.

11. The nozzle of claim 1, wherein the collar has a wall thickness that is greater than a wall thickness of the skirt.

12. The nozzle of claim 1, wherein the tip of the nozzle defines a substantially planar surface.

13. The nozzle of claim 12, wherein the planar surface of the tip is substantially perpendicular to the center axis of the nozzle.

14. The nozzle of claim 1, wherein the plurality of facets comprises at least two frustum sections stacked in series on top of one another, wherein a first frustum section has an average diameter that is larger than an average diameter of a second frustum section.

15. The nozzle of claim 14 further comprising a ridge located at a first inflection point between the first frustum section and the second frustum section.

16. The nozzle of claim 1, wherein the plurality of facets comprises five stepped sections stacked in series on top of one another, wherein a first stepped section at a base of the skirt has an average diameter that is larger than each respective average diameter of each remaining stepped section.

17. The nozzle of claim 16 further comprising at least four ridges disposed on the outer surface of the skirt, wherein one of the ridges is provided at an intersection of each of the stepped sections.

18. The nozzle of claim 1 further comprising a recessed groove defined within a bottom of the skirt, wherein the recessed groove has a diameter smaller than a diameter of a terminal edge of the skirt.

19. The nozzle of claim 18 further comprising a flange extending from the recessed groove, wherein the flange has a diameter larger than the diameter of the recessed groove.

20. The nozzle of claim 19, wherein the diameter of the flange is larger than the diameter of the terminal edge of the skirt.

21. The nozzle of claim 20, wherein the flange and the recessed groove are configured to secure the nozzle to a body forming the reservoir.

* * * * *